US008589316B2

(12) United States Patent
Lujan et al.

(10) Patent No.: US 8,589,316 B2
(45) Date of Patent: Nov. 19, 2013

(54) SYSTEM AND METHOD TO ESTIMATE REGION OF TISSUE ACTIVATION

(75) Inventors: J. Luis Lujan, Cleveland, OH (US); Ashu Chaturvedi, Cleveland, OH (US); Cameron C. McIntyre, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 277 days.

(21) Appl. No.: 12/869,159

(22) Filed: Aug. 26, 2010

(65) Prior Publication Data

US 2011/0191275 A1  Aug. 4, 2011

Related U.S. Application Data

(60) Provisional application No. 61/237,375, filed on Aug. 27, 2009.

(51) Int. Cl.
*G06F 15/16* (2006.01)

(52) U.S. Cl.
USPC .......................................................... 706/12

(58) Field of Classification Search
USPC .......................................................... 706/12
See application file for complete search history.

(56) References Cited

U.S. PATENT DOCUMENTS

| 2006/0017749 | A1 | 1/2006 | McIntyre et al. | |
| 2007/0083104 | A1* | 4/2007 | Butson et al. | 600/407 |
| 2007/0288064 | A1* | 12/2007 | Butson et al. | 607/45 |
| 2008/0300797 | A1* | 12/2008 | Tabibiazar et al. | 702/19 |

OTHER PUBLICATIONS

Patient-specific analysis of the volume of tissue activated during deepbrain stimulation Christopher R. Butson, Scott E. Cooper, Jaimie M. Henderson,c and Cameron C. McIntyrea.*
Role of electrode design on the volume of tissue activated during deep brain stimulation; DBS electrode design, Journal of Neural Engineering, Institute of Physics Publishing, Bristol, GB LNKD-DOI:1088/1741-2560/3/1/001, vol. 3, No. 1, Mar. 1, 2006.
Subthalamic Nucleus Deep Brain Stimulation: Accurate Axonal Threshold Prediction with Diffusion Tensor Based Electric Field Models, Engineering in Medicine and Biology Society, 2006. EMBS' 06 28th Annual International Conference of the IEEE, IEEE, Piscataway, NJ USA, Aug. 30, 2006.
Predicting the Effects of Deep Brain Stimulation with Diffusion Tensor Based Electric Field Models Jan. 1, 2001, Medical Image Computing and Computer-Assisted Intervention—MIC CAI 2006 Lecture Notes in Computer Science; LNCS, Springer, Berlin, DE.
International Search Report and The Written Opinion of the International Searching Authority, from related International Application No. PCT/US210/046772, mailed Nov. 23, 2010.

* cited by examiner

*Primary Examiner* — Kakali Chaki
*Assistant Examiner* — Ababacar Seck
(74) *Attorney, Agent, or Firm* — Kenyon & Kenyon LLP

(57) ABSTRACT

A computer-implemented method for determining the volume of activation of neural tissue. In one embodiment, the method uses one or more parametric equations that define a volume of activation, wherein the parameters for the one or more parametric equations are given as a function of an input vector that includes stimulation parameters. After receiving input data that includes values for the stimulation parameters and defining the input vector using the input data, the input vector is applied to the function to obtain the parameters for the one or more parametric equations. The parametric equation is solved to obtain a calculated volume of activation.

21 Claims, 10 Drawing Sheets

SYSTEM AND METHOD TO ESTIMATE REGION OF TISSUE ACTIVATION

GOVERNMENT FUNDING

This invention was made with government support under Grant No. NIH R01 NS059736. The U.S. government has certain rights in the invention.

RELATED APPLICATIONS

This application claims the benefit of U.S. Provisional Application Ser. No. 61/237,375 (filed on 27 Aug. 2009), which is incorporated by reference herein.

This application is also related to U.S. patent application Ser. No. 11/606,260, filed Nov. 28, 2006, and entitled SYSTEM AND METHOD TO DESIGN STRUCTURE FOR DELIVERING ELECTRICAL ENERGY TO TISSUE, which claims the benefit of U.S. provisional patent application No. 60/740,031 which was filed on Nov. 28, 2005, and entitled "Role of electrode design on the volume of tissue activated during deep brain stimulation." U.S. patent application Ser. No. 11/606,260 is also a continuation-in-part application of U.S. patent application Ser. No. 10/885,982, now U.S. Pat. No. 7,346,382, filed Jul. 7, 2004, and entitled "BRAIN STIMULATION MODELS, SYSTEMS, DEVICES, AND METHODS." This application is also related to U.S. provisional patent application No. 61/120,006, filed Dec. 4, 2008, and entitled SYSTEM AND METHOD TO DEFINE TARGET VOLUME FOR STIMULATION IN BRAIN. The entire contents of each of the above-identified applications are incorporated herein by reference.

TECHNICAL FIELD

The present invention relates generally to systems and methods for estimating a region of tissue activation, such as for stimulation in a patient's brain or spinal cord.

BACKGROUND

Electrical stimulation of the nervous system has provided a therapeutic treatment for a variety of disorders. For example, electrical stimulation has been applied to pain management, such as by performing stimulation of the spinal cord. Electrical stimulation has also been performed to augment hearing in the context of cochlear implants. Deep brain stimulation (DBS) has become an established therapy for treating various conditions including, for example, Parkinson's disease and dystonia. DBS has also been employed to treat several other conditions, such as clinical depression, obsessive compulsive disorder, and epilepsy to name a few.

By way of further example, the discovery that high frequency DBS generates clinical benefits analogous to those achieved by surgical lesioning has transformed the use of functional neurosurgery for the treatment of movement disorders. In first world countries, thalamic DBS for intractable tremor has replaced ablative lesions of the thalamus, and DBS of the subthalamic nucleus or globus pallidus internus (GPi). GPi has replaced pallidotomy in the treatment of the cardinal motor features of Parkinson's disease (e.g., tremor, rigidity, bradykinesia). In addition, GPi DBS has emerged as an effective therapy for dystonia, and the utility of DBS is being examined for the treatment of epilepsy, obsessive-compulsive disorder, Tourette's syndrome, and major depression.

Despite the documented clinical successes of neurostimulation, the mechanisms and effects of neurostimulation at the neuronal level remain difficult to predict. As a result, modeling and simulation have played increasingly important roles in the engineering design and scientific analysis of neurostimulation.

SUMMARY

The invention relates generally to systems and methods for estimating a region of tissue activation, such as associated with stimulation in a patient's neural tissue (e.g., brain or spinal cord).

In one embodiment, an artificial neural network (ANN) is programmed to output parameters of a mathematical expression that corresponds to an estimated volume of tissue activation (VTA) for a set of input parameters (electrode configuration, stimulation parameters). A given ANN can determine the estimated VTA for different for electrode configurations and stimulation parameters for which no simulations or clinical studies have been performed. Additionally, the ANN can be trained to provide the estimated VTA for a plurality of different types of electrodes without requiring retraining of the ANN for the different types of electrodes.

In another embodiment, the present invention provides a computer-implemented method for determining the volume of activation of neural tissue, comprising: (a) having one or more parametric equations that define a volume of activation, wherein the parameters for the one or more parametric equations are given as a function of an input vector that includes stimulation parameters; (b) receiving input data that includes values for the stimulation parameters and defining the input vector using the input data; (c) applying the input vector to the function and obtaining the parameters for the one or more parametric equations; and (d) solving the parametric equation to calculate the volume of activation. The calculated volume of activation may be displayed on a display screen.

In another embodiment, the present invention provides a method for determining a function that outputs the parameters of one or more parametric equations that define a volume of activation, comprising: (a) having an electric field model of an electrode and a neural tissue model; (b) coupling the electric field model to the neural tissue model to obtain volumes of activation for multiple different sets of stimulation parameters and electrode configuration parameters; (c) fitting a geometric shape to the volumes of activation, wherein the geometric shape is defined by one or more parametric equations; and using a computational training algorithm to design a function that correlates the different sets of stimulation parameters and electrode configuration parameters to the parameters for the one or more parametric equations that represent the geometric shapes that are fitted to the volumes of activation. In another embodiment, the present invention provides a non-transitory computer-readable storage medium comprising instructions for determining the volume of activation using one or more parametric equations whose parameters are given as a function of an input vector that includes stimulation parameters and electrode configuration parameters, wherein the function is obtained by this method.

DETAILED DESCRIPTION

Figure 1:
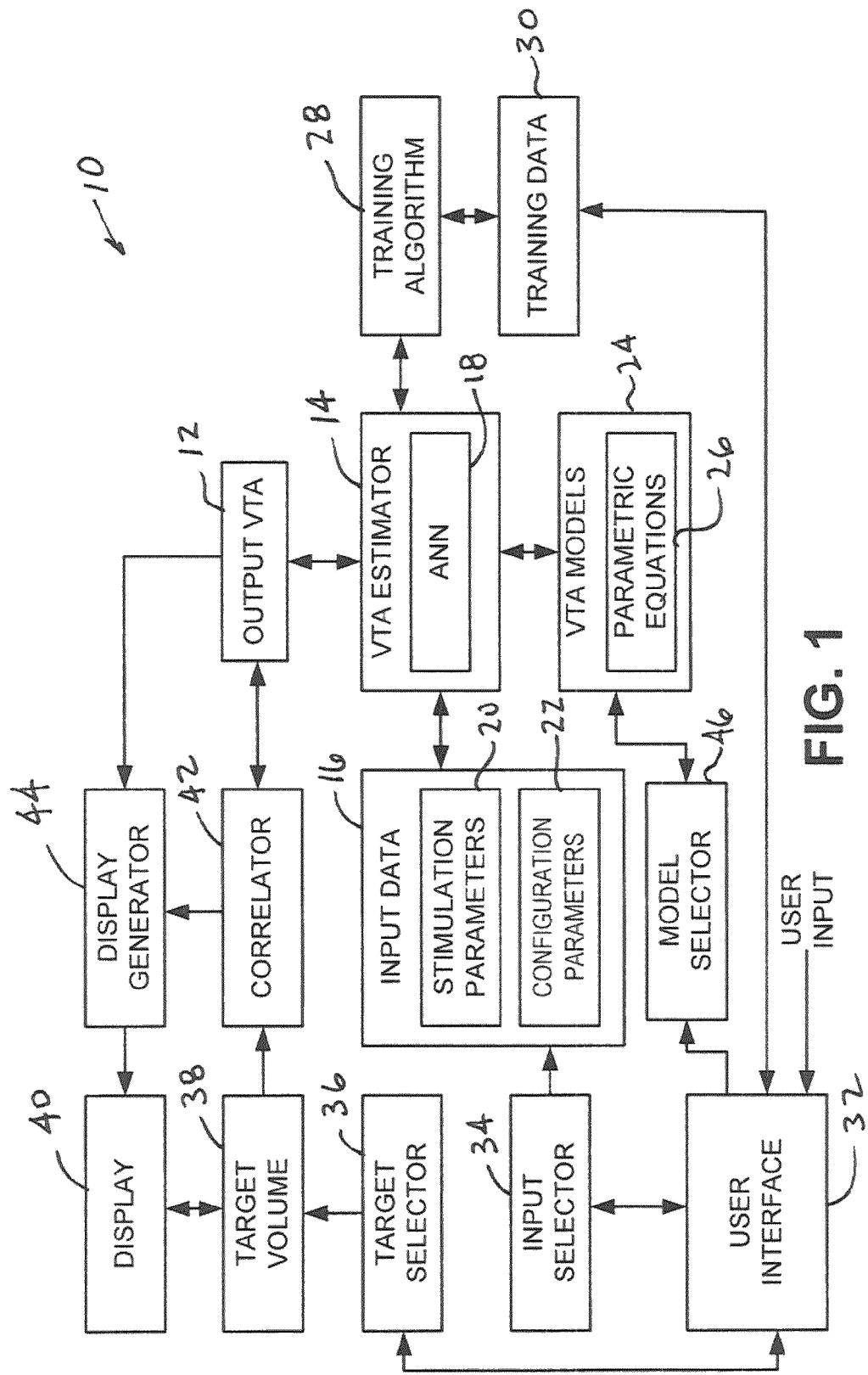
FIG. 1 depicts a functional block diagram of an example approach that can be employed to determine a volume of tissue activation according to an aspect of the invention.

The invention relates generally to systems and methods for estimating or predicting a volume of neural tissue (for example, in the brain or spinal cord) activated by electrical stimulation. FIG. 1 depicts an example of a system 10 that can be implemented to estimate a volume of neural tissue activated, indicated as an output volume of tissue activation (VTA) 12. The system 10 includes a VTA estimator 14 that is programmed to provide the output VTA for a set of input data 16. The VTA estimator 14 can employ artificial intelligence and/or machine learning techniques (e.g., artificial neural networks, function predictors, expert systems or the like).

In the example of FIG. 1, the artificial intelligence component of the VTA estimator 14 is depicted as being artificial neural network (ANN), although it would be understood and appreciated other techniques and methodologies could be utilized based on teachings herein. The ANN 18 is trained to provide the output VTA 12 in response to the input data 16 according to the complex relationships between the input data 16 described or modeled by the ANN 18.

The input data 16 includes stimulation parameters 20 and configuration parameters 22. Collectively the stimulation parameters 20 and configuration parameters 22 can define an input vector, based on which the output VTA 12 is to be calculated. It will be understood and appreciated that the particular number of dimensions for the input vector can vary according to application requirements and capabilities of a corresponding ANN 18. The input stimulation parameters 20, for example, can include an indication whether the stimulation is activated by voltage or current control device. The input data 16 can also include stimulation parameters 20, such as voltage or current amplitude, frequency, pulse width and pulse shape.

The electrode configuration parameters 22 can define structural characteristics, such as dimensions and configurations and interrelationships for an electrode design. The configuration can be set for commercially available electrode designs or to a custom design. For the example of an electrode having a plurality of cylindrical electrode contacts, the electrode configuration parameters 22 can include the height, diameter and spacing (or distribution) of the electrode contacts along the electrode shaft. Relationships between parameters can also be represented in the input data 16, such as the aspect ratio (d/h). The aspect ratio further can be utilized to constrain the optimization procedure, such as by limiting the search space to a predefined range of aspect ratios (e.g., d/h<some predefined value).

Additionally, the stimulation parameters 20 and the configuration parameters 22 can be interrelated. For instance, a given configuration of electrode can have any number of one or more electrode contacts, corresponding stimulation parameters 20 may thus be provided for stimulation of the one or more electrode contacts. Additionally, the stimulation parameters can define whether a given contact is an anode or cathode. It will be appreciated that a given set of input data (e.g., stimulation and configuration parameters) corresponds to a given output VTA 12. Thus there can be any number of input data 16, which can be varied to provide corresponding output VTAs, as described herein.

The ANN 18 can employ VTA models 24 to mathematically represent or describe a region, which can be an area (e.g., in two dimensions) or volume (e.g., in three dimensions) for the activated region of tissue represented in the output VTA 12. Thus the VTA models 24 can include a set of one or more parametric equations 26 which can be utilized individually or in any combination thereof in the ANN 18 for use in computing the output VTA 12 based on the input data 16.

Figure 2:
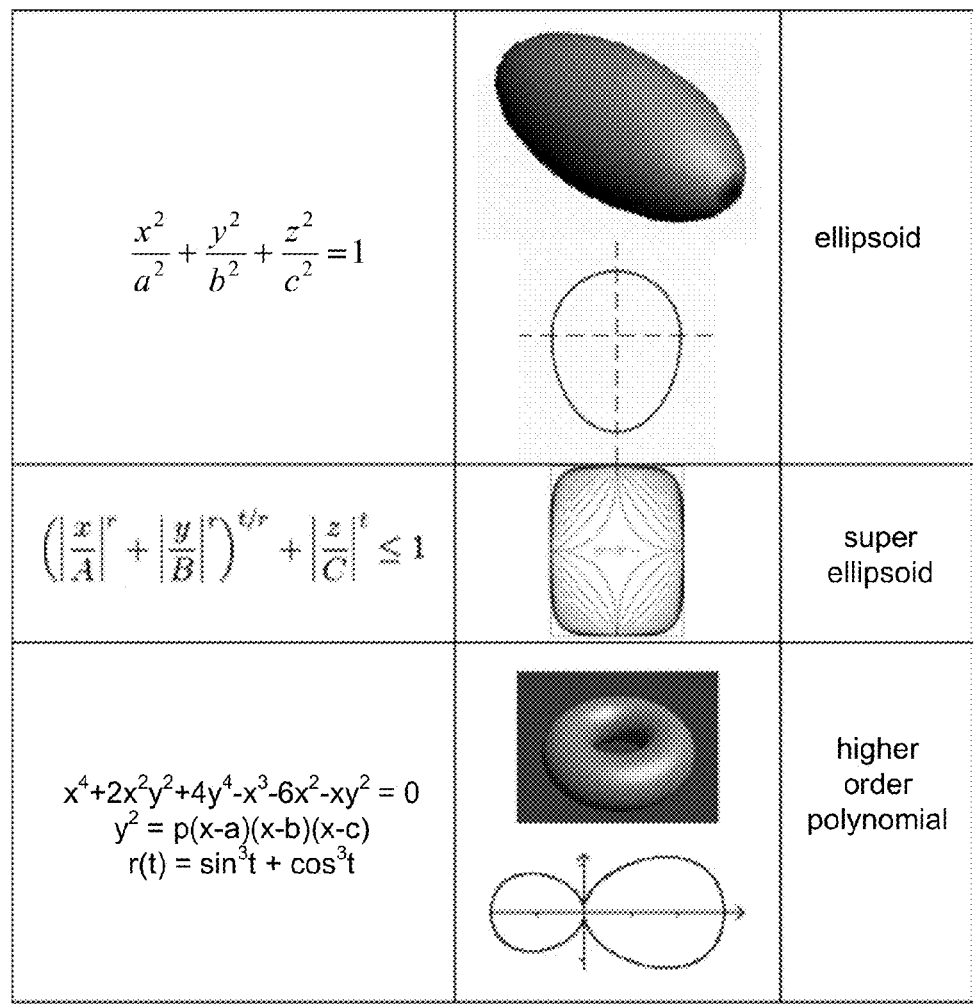
FIG. 2 depicts an example of models that can be utilized to describe a region of tissue activated.

FIG. 2 depicts examples of some parametric equations 26 that can be utilized by the VTA estimator 14. In the example of FIG. 2, parametric equations are illustrated for an ellipsoid, a super ellipsoid as well as for higher order polynomials. It will be understood and appreciated other shapes and parametric equations and combinations thereof can be utilized as VTA models 24. In the example equations in FIG. 2, A and B are the equatorial radii (along the x and y axis, respectively) and C is the polar radius along the Z axis. The parameters r and t with respect to parametric equations control the amount of flattening at the tips at the equator.

It will be understood and appreciated that the center of each geometric volume described by the parametric equations 26 can represent an active region which may or may not be at the center of the active contacts in the electrodes being modeled thereby. The particular center of the contacts and the center of the active regions may differ depending on, for example, the stimulation and configuration parameters (e.g., the contact configuration on the voltage, electrode type pulse width, impedance or other stimulation or configuration parameters) 20 and 22, respectively.

The VTA estimator 14 can utilize any number of one or more artificial neural networks (ANN) 18. By further example, the VTA estimator 14 can estimate the parameters of the mathematical parameters for the parametrical equations 26 defining the volumes of neural tissue activated without having to perform neuronal model simulations or refit equations to a given activation spread.

Figure 3:
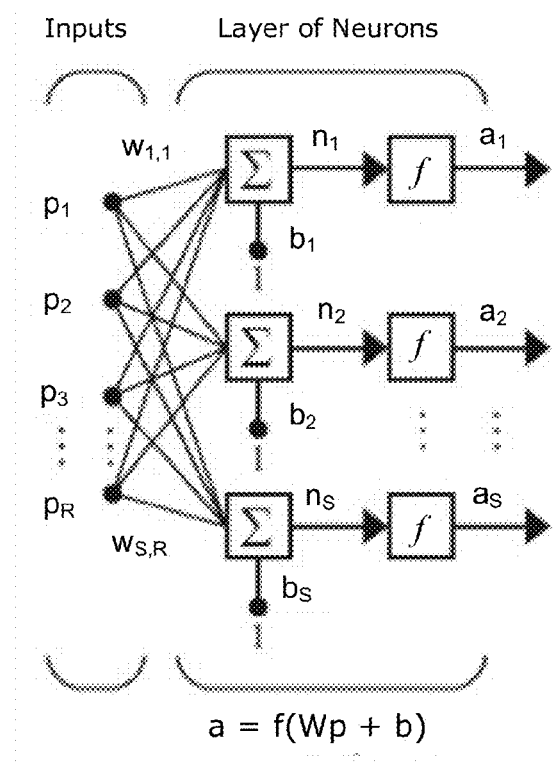
FIG. 3 depicts an example of an artificial neural network that can be implemented.

As a further example, the VTA estimator 14 can employ one or more artificial neural networks, such as two-layer neural networks depicted in FIG. 3 (see, e.g., Mathworks Neural Network Toolbox, www.mathworks.com/access/helpdesk/help/pdf_doc/nnet/nnet.pdf), to create VTA predictors programmed to estimate the parameters of the mathematical equation(s) 26 defining the volumes of neural tissue activated. Advantageously, the estimation can be implemented without having to perform neuronal model simulations or re-fit the equations to the activation spread. As one example case where VTAs are modeled with ellipsoids, the VTA estimator 14 can be implemented with a pair of two-layer neural networks with sigmoid and linear transfer functions in the hidden and output layers, respectively.

Examples of sigmoid transfer function that can be utilized in the layers of the ANN 18 are described in Narendra K. S., Parthasarathy K. (March 1991) "Gradient methods for the optimization of dynamical systems containing neural networks", IEEE Transactions on Neural Networks, Vol. 2, No. 2, 252-262. Examples of linear transfer function that can be utilized in the layers of the ANN 18 are described Jonic S., Jankovic T., Gajic V., Popovic D. (March 1999) "Three machine learning techniques for automatic determination of rules to control locomotion", IEEE Trans. On Biomedical Engineering, Vol. 46, No. 3, 300-310.

Continuing with the example of two ANNs 18, one ANN can contain 12 inputs (e.g. representing pulsewidth, impedance, configuration number, voltage amplitude, contact configuration, active ellipsoids), 20 hidden neurons, and 8 output neurons (a0, c0, a1, c1, a2, c2, a3, c3) that define the ellipsoid parameters (b=a due to axi-symmetric properties of model). The architecture of the second ANN 18 can be the same as the first, but the outputs were the centers of up to four VTAs or active regions along the vertical axis of the electrode shaft (z0, z1, z2, z3). Those skilled in the art will understand and appreciate various types of transfer functions (other than the sigmoidal and linear functions described above) and any numbers of layers that can be utilized to implement the ANN 18.

The ANN 18 can be pre-trained on the system 10 such with a set of training data 30 so that the ANN is valid for generating the output VTA 12 over a range of the input parameters 16. The system 10 can also be trained for a given application or retrained in the event that a user wishes to expand the range of the VTA estimator to accommodate additional input data outside the range of the original training of the ANN 18.

The system 10 can include a training algorithm 28 that can retrain the ANN 18 based on the set of training data 30. The training data 30 can be pre-processed or normalized to provide a normalized set of training data 32 according to the requirements of the ANN 18. For instance, the training data 30 can be obtained using computer simulations of axonal cable models.

The training algorithm 28 can implement back propagation or propagation of error based on applying the training data 30 to desired output data using the ANN 18. As one example, each ANN 18 can be trained (or retrained) using the Levenberg-Marquardt and the gradient decent with momentum algorithm. Examples of possible training algorithms according to these methods are disclosed in the following: Gill P. R., Murray W., Wright M. H. (1981) "The Levenberg-Marquardt Method" in Practical Optimization. London: Academic Press, 136-137; Levenberg K. (1944) "A Method for the Solution of Certain Problems in Least Squares" Quart. Appl. Math. Vol. 2, 164-168; and Marquardt D. (1963) "An Algorithm for Least-Squares Estimation of Nonlinear Parameters" SIAM J. Appl. Math. Vol. 11, 431-441.

As an example for initial training, some or all of the available input/output data corresponding to actual stimulation cases, which has been utilized to determine VTAs, can be utilized to train the VTA estimator 14. A subset of the available cases can be used as validation data to avoid over-fitting, and yet another subset or the remaining cases can be utilized to estimate the generalization error. The neural network weights and biases can be initialized randomly. Each ANN 18 can be trained until the normalized fitting mean squared error (MSE) reached a predetermined value (e.g., less than 1e-5), until the validation error increased with respect to the fitting error, or for a maximum of number (e.g., 1000) of epochs.

After the VTA estimator 14 has been programmed such as by training the ANN 18, the system 10 can then be utilized to generate output VTA 12 for a set of the input data 16. To facilitate such process, the system 10 can include a user interface 32 which can include a variety of buttons, drop down menus or other graphical and text based user interface elements, as is known in the art. The user interface 32, for example, can be utilized to provide or access a set of input data 16 or otherwise define a method of operation or mode of operation to be implemented by the system 10.

The generalized relationships between the input data vector 16 and output VTA 12 is achieved through trained artificial neural networks. To calculate the parameters of the mathematical equation (s) that define a VTA, a series of simple equations can be solved. As one example, the equations can have the following form:

$$I_N = \frac{2I - \max(I_T) - \min(I_T)}{\max(I_T) - \min(I_T)}$$

$$HL = IW \cdot I_N + b_1$$

$$o_1 = \frac{1}{1 + e^{-NL}}$$

$$o_2 = LW \cdot o_1 + b_2$$

$$\text{output} = \frac{o_2[\max(T_T) - \min(T_T)] + \max(T_T) + \min(T_T)}{2}$$

Where n is the number of hidden neurons;
m is the number of network outputs;
I is the 12×1 input vector for which we want to calculate the VTA;
$\max(I_T)$ and $\min(I_T)$ define the maximum and minimum values, respectively, that the inputs can achieve;
IW are the n×12 input weights;
b1 is the n×1 input bias vector;
o1 is a n×1 vector that contains the output from the input layer. LW and b2 are the m×n matrix of weights and m×1 vector of biases, respectively, for the hidden layer;
o2 is the m×1 normalized output vector;
$\max(T_T)$ and $\min(T_T)$ are the m×1 vectors that define the maximum and minimum values, respectively, that the outputs can achieve; and
output is the m×1 vector of parameters that define the VTA.

Referring back to FIG. 1, the system 10 can also include a model selector 46 that is operative to select one or more VTA models 24. The model selector 46 can be implemented manually, such as in response to user input received via the user interface 32. Alternatively, the model selector 46 can be implemented as an automatic process that is programmed to select an appropriate one or more of the parametric equations based on the input data. For instance, the model selector 46 can employ a constrained optimization algorithm to minimize a cost function formed by multiple (e.g., three) components and ensure maximum fit between the parametric equations 26 and the spread of fiber activation corresponding to the VTA. As a further example, a first cost function component can correspond to the difference between the most distal edges (on both the horizontal and vertical planes) of our parametric equation and the 2D contour. A second component can correspond to the perimeter-length difference between the area covered by the parametric equation and the 2D contours. A third component can correspond to the difference in area covered by the parametric equation and by the 2D active fiber contour.

In one example embodiment, a constrained optimization on the data can be performed using the Matlab® Optimization Toolbox's fmincon function (The MathWorks Inc., Natick, Mass.), although other commercially available or proprietary methods can be utilized. This optimization method finds a minimum of a constrained nonlinear multivariable function using Sequential Quadratic Programming (SQP) [Coleman and Zhang 2006]. SQP is described in detail in the following: Powell M. J. D., (1983) "Variable Metric Methods for Constrained Optimization," Mathematical Programming: The State of the Art, (A. Bachem, M. Grotschel and B. Korte, eds.) Springer Verlag, 288-311; Fletcher R., (1987) "Practical Methods of Optimization," John Wiley and Sons; Gill P. R., Murray W., Wright M. H. (1981) "The Levenberg-Marquardt Method" in Practical Optimization. London: Academic Press, 136-137; and Hock W., Schittkowski K., (1983) "A Comparative Performance Evaluation of 27 Nonlinear Programming Codes," Computing, Vol. 30, 335. Those skilled in the art will understand and appreciate other commercially available and proprietary tools and software that can be utilized for selection of appropriate parametric equations 26.

Each active area thus can be described by one of the parametric equations (e.g., ellipsoids, super ellipsoids, second or higher order polynomials, etc.) or combination of any two or more parametric equations, such as shown in FIG. 2. While three parametric equations are depicted in FIG. 2, those skilled in the art will appreciate that other numbers and shapes can be utilized as parametric equations.

By way of further example, the user interface can invoke an input selector 34 to define one or more set of input data 16, such as including the stimulation parameters and/or the configuration parameters 20 and 22. Alternatively, the input selector 34 can be utilized to select an input mode, such as to set the system for determining a set of input data that can be utilized to provide a desired target VTA. The system 10 can also include a target selector 36 that is utilized to define and/or set a desired target volume of tissue to be activated 38. The target volume 38 can be selected via the user interface, such as corresponding to a 2-D and/or 3-D representation, which may be presented on a corresponding display 40. For example, the display 40 can provide a three dimensional or two dimensional representation of an anatomical region such as the brain in which the target volume resides. The 3-D model presented on the display can correspond to a general model of brain anatomy. Alternatively, the model represented on the display 40 can correspond to a patient-specific model, such as can be generated using a corresponding imaging modality (e.g., CT scan or MRI or the like).

Where a target volume 38 has been selected via the target selector 36, the system 10 can employ a correlator 42 that is programmed to perform mathematical correlation between the target volume and the output VTA 12. The correlator 42 can perform correlation between the output VTA 12 and the target volume 38 to calculate a volume or area of overlap between the output VTA and the model volume represented by the target VTA. As one example, the correlator 42 can be programmed to perform a constrained optimization algorithm. The corresponding results can be sent to a display generator 44 and in turn reproduced for visual presentation (and comparison) on the display 40.

Where the system 10 is being utilized to determine a set of input data 16 to achieve a corresponding target volume 38 that has been selected, the input selector 34 can vary the stimulation and/or configuration parameters 20 and 22 over a range of available settings. Each corresponding output VTA can be correlated by the correlator 42 relative to the target volume 38 and provided a score indicative of the amount of overlap. The VTAs 12 and 38 and their scores can be displayed to a user, such as by providing corresponding data to the display 40 or other output device (e.g., a printer). The output VTA having a maximum amount of overlap relative to the target volume can be determined and the corresponding input data provided as an output on the display or to another output device (not shown).

The given set of input data thus can represent a particular structure for an electrode as well as stimulation parameters, which can be utilized to achieve the desired target VTA. The system 10 may also provide a graphical representation on the display 40 of an electrode design corresponding to the configuration parameters 22 for the output VTA. The electrode design can be a commercially available design or a custom design. It will be appreciated that there can be more than one target VTA and thus more than set of input data for a given patient.

It will be further appreciated that for each of the different sets of input data (e.g., including stimulation parameters and configuration parameters) the trained ANN 18 can be utilized for rapid evaluation of the respective designs to ascertain design and stimulation parameters without having to retrain or perform additional simulations for clinical measurements. Accordingly, those skilled in the art will understand and appreciate that the system 10 and the VTA estimator 14 can be utilized to assist the interoperative planning of electrode tracks or deep brain stimulation (DBS) or other stereotactic surgery by helping to identify an implant location for the DBS electrodes. This could be utilized by adjusting the target volume with respect to an accordance system in the user and determining the output VTA 12 at each respective location and for different simulation parameters until a best match is found.

The system 10 can also include one or more other input or output devices (not shown). Such devices can provide an interface through which a user can input data as well as control the methods. For example, a user can employ the I/O device to input data, such as instructions to initiate or modify the electrode design procedure. Alternatively, the I/O device can be employed to acquire the training data 30, such as from a location in local memory, from another storage location, or to access another process running on another computer.

EXPERIMENTAL

The following discussion relates to activities of the inventors that include experiments and procedures that provide a foundation for the concepts described herein, including procedures used for determining parametric equations and VTAs for training data suitable for use in an ANN.

Figure 8:
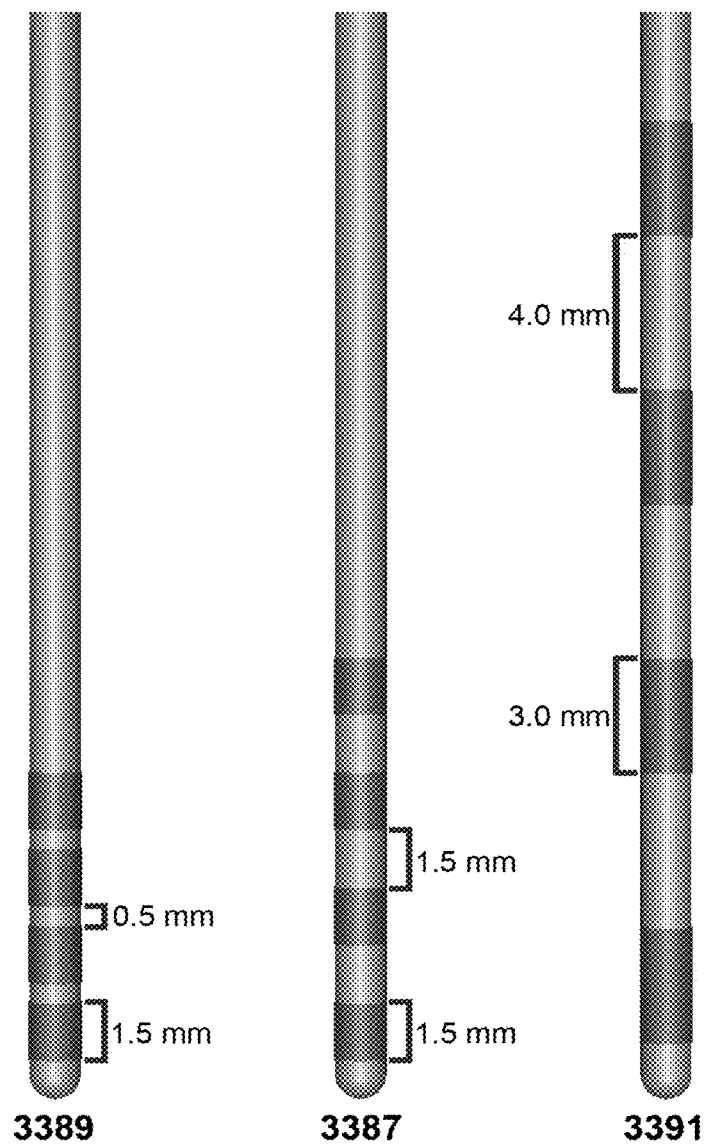
FIG. 8 depicts the electrode configuration for three Medtronic electrodes used in the computational trials.

A computational model of deep brain stimulation was created to estimate the spatial spread of neural activation within the brain and characterize the volumes of tissue activated. This computational of deep brain stimulation had both anatomical and electrical components. The electrical components included three virtual electrodes created from geometric representations of Medtronic deep brain stimulation electrodes (model numbers 3389, 3387, and 3391; Medtronic, Minneapolis, Minn.), as shown in FIG. 8.

Electric Field Model

The computational modeling studies included a model of a virtual electrode inserted inside brain tissue. The virtual electrodes were modeled to represent Medtronic 3389, 3387, and 3391 deep brain stimulation electrodes (see FIG. 8). For each virtual electrode, over 150 axi-symmetric, multi-resolution, finite element models (FEM) were created to model the electric field within the brain tissue. The FEMs were created using COMSOL (Comsol Inc., Burlington, Mass.) and SCIRun 3.3 (Scientific Computing and Imaging Institute, Salt Lake City, Utah), and included representations of the virtual electrode, the electrical conductivity of brain tissue surrounding the electrode, capacitance at the electrode-tissue interface, a thin layer of encapsulation tissue around the electrode, and stimulation settings typically used in clinical applications.

The electrodes were represented as purely capacitive elements with a 3.3 µF (for the Medtronic 3387 and 3389 electrodes) or 6.6 µF (for the Medtronic 3391 electrode) capacitance to reflect the contact size. The brain tissue was represented as a homogeneous, isotropic medium having a bulk conductivity of 0.3 S/m. The model also incorporated a 0.5 mm thick encapsulation layer surrounding the electrode to account for charge transduction reactions and a 42% voltage drop at the electrode-tissue interface. The conductivity of the encapsulation layer in each model was adjusted to match the target impedance. A range of stimulation settings and electrode configurations (see Table 1 below) were applied to the electric field model and a Fourier FEM solver was used to solve Poisson's equation with Dirichlet and Neumann boundary conditions. The ground conditions of the electric field model were the boundaries of the FEM mesh if there were no anodes present during stimulation, or the anode(s) if they were present.

TABLE 1

| | |
|---|---|
| Electrodes: | 3389, 3387, 3391 |
| Frequency: | 130 Hz |
| Pulse-widths: | 60, 90, 120, 150, 180, 210, 450 µs |
| Amplitudes: | 1, 2, 3, 4, 5, 6, 7, 8, 9, 10 V |
| Impedances: | 0-749, 750-1250, 1251+ Ω |
| Contact configurations: | 15 monopolar, 12 bipolar, 28 tripolar, 10 quadripolar |

Neural Tissue Model

Figure 4:
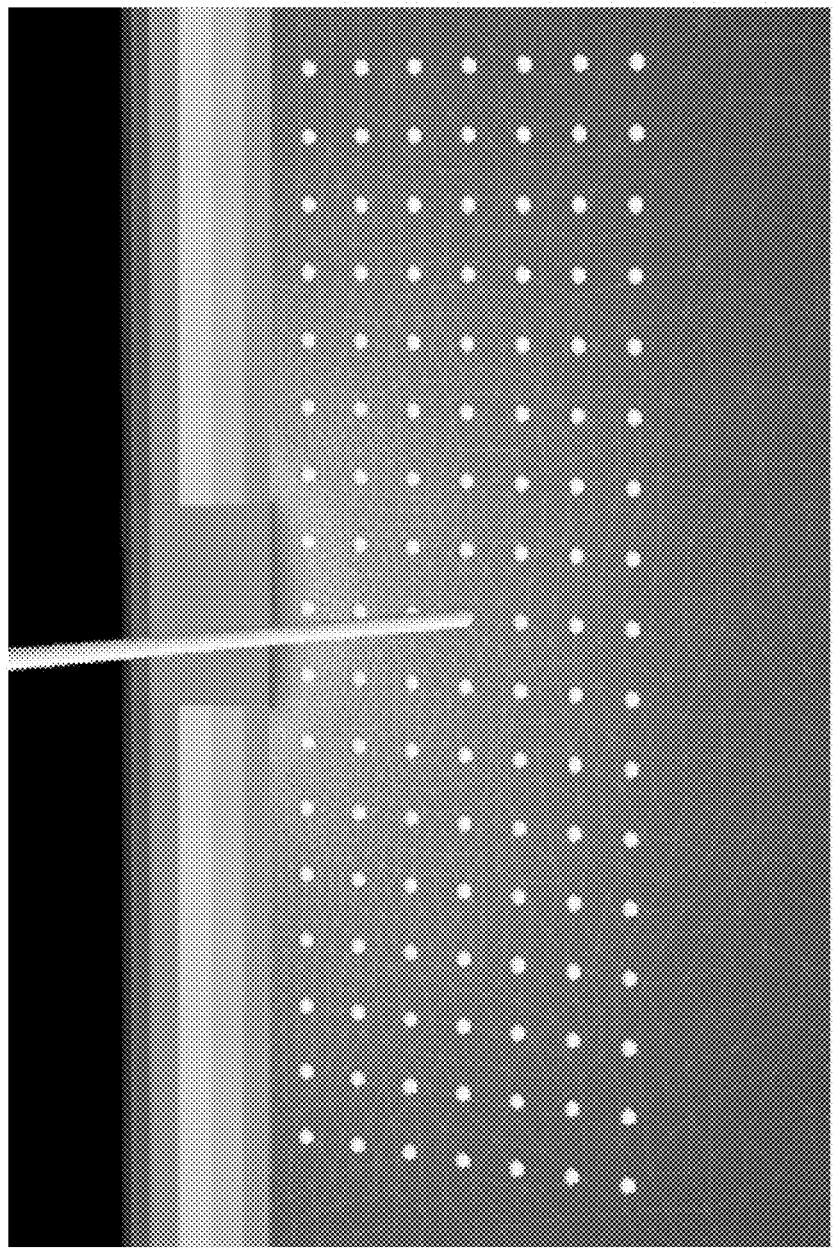
FIG. 4 depicts an example of an axon model and electrode structure that can be utilized to identify a region of tissue activated.
Figure 9:
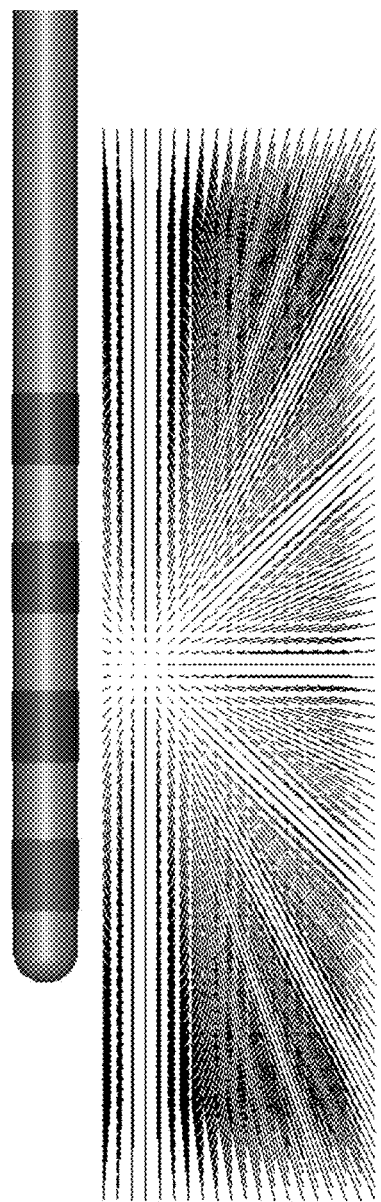
FIG. 9 depicts a Medtronic 3387 electrode in an axi-symmetric finite element model with the axon fibers oriented perpendicular to the electrode shaft.

The electric field model was coupled to a neural tissue model to determine neuronal activation. As shown in FIG. 9, the neural tissue model had over 2,500 trajectories of white matter axon fibers which were distributed in a matrix perpendicular to the electrode shaft with an inter-fiber resolution of 0.2 mm along the vertical (dorsal-ventral) and horizontal (medial-lateral) axes. The axon population was positioned about 0.7 to 11.0 mm lateral to the electrode shaft, and −7.0 to +32.0 mm above the tip of the electrode. FIG. 4 shows another illustration of how the axons can be arranged in a matrix adjacent the electrode shaft. A multi-compartment model of a myelinated axon was created to represent each of these axons. Axonal parameters for these models were defined according to McIntyre et al. for 5.7 µm axons (McIntyre et al., J Neurophysiol. 2002 February; 87(2):995-1006). The geometry required to explicitly define the trajectory of each axon was determined using Matlab (Mathworks Inc., Natick, Mass.). Because of the perpendicular orientation of the axons, the spread of activation relative to the electrode shaft could be determined.

The extracellular voltages along each axon model was determined by interpolating each electric field onto each axon compartment. The axonal behavior in response to extracellular stimulation was simulated for all axon models and each of the electric field FEMs using the NEURON simulator. In this simulation, an axon was considered activated if it fired an action potential in response to the applied electric field simulation.

The activated fibers were grouped into active regions. For simplicity, active regions for each active electrode contact (cathode or anode) on the virtual electrode were defined. Each activated fiber was assigned to the nearest active region by its distance from the center of each fiber to the center of each electrode contact. Each active region could have more than one contact, but a given contact could only belong to a single active region. As such, each active region was defined as either cathodic or anodic, depending on the nature of its corresponding electrode contact. If an activated fiber was equidistant to a cathode and an anode, the fiber was considered to be activated by the cathode. In some cases, adjacent active regions were merged into a single active region depending upon the electrode configuration and symmetry.

Figure 5:
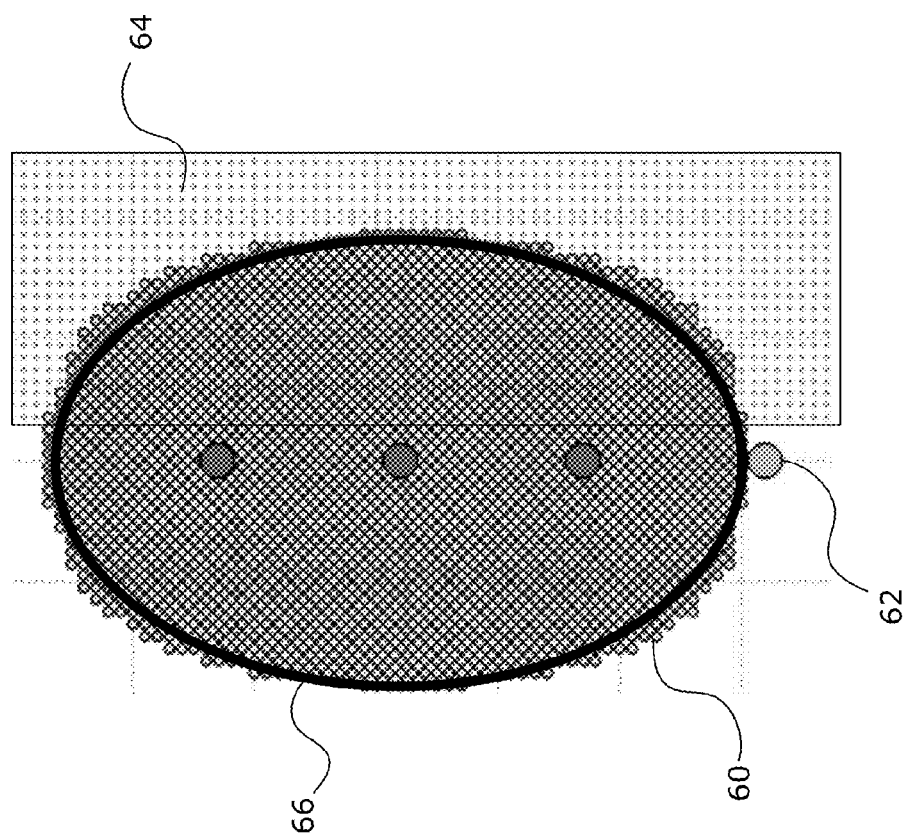
FIG. 5 depicts an example of a region of tissue activated for a first set of stimulation parameters and configuration parameters.
Figure 6:
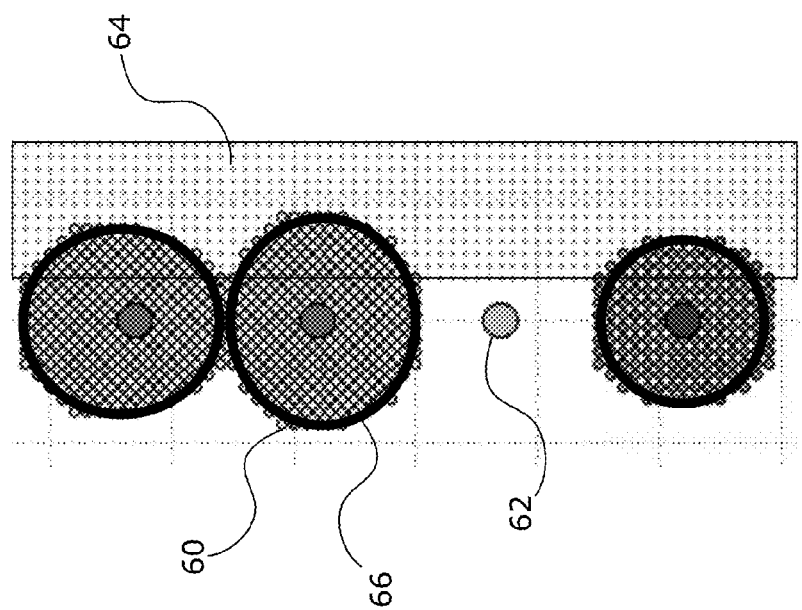
FIG. 6 depicts an example of a region of tissue activated for a second set of stimulation parameters and configuration parameters.
Figure 11:
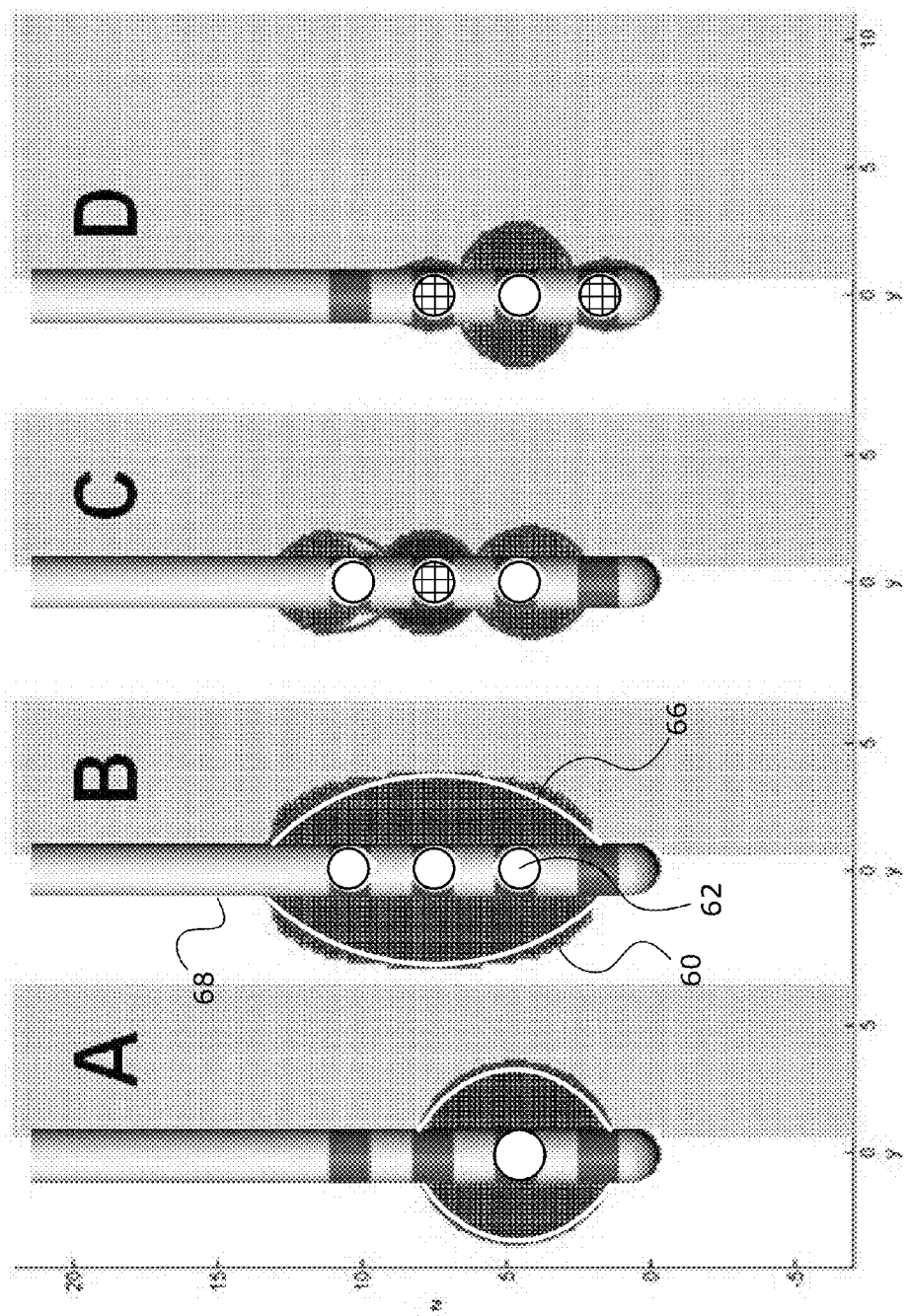
FIG. 11 depicts an example of regions of tissue activated by different configurations for electrode contact activation.

The two-dimensional boundaries of each active region were defined by a parametric equation for an ellipse that best encompassed the spread of activated fibers within its horizontal and vertical planes. A constrained optimization algorithm was used to find the parameters of this parametric equation that minimized the root mean squared (RMS) error between the actual boundaries of the active region and the geometric outline defined by the parametric equation. The upper and lower bounds were defined by obtaining the maximum lateral and vertical distances from each active fiber to the center of the active region. Because this was an axi-symmetric stimulation model, the 2D elliptical outline generated by the parametric equation could be rotated around the electrode shaft (z-axis) to create a three-dimensional VTA. FIGS. 5 and 6 depict examples of active regions 60 that can be determined by measuring the spread of the fibers 64 in each active region 60. The elliptical outline 66 of each active region 60 are 2D contours on a plane parallel to the electrode contacts 62 and centered on the electrode shaft. The edges 66 define an ellipse that has been optimally fitted to its respective active region 60. FIG. 11 shows another example of active regions 60 under different configurations for electrode contact activation. The elliptical outlines 66 of the parametric equation fitted to the active regions 60 are shown as a white lines around active regions 60. On the electrodes 68, active contacts 62 that are cathodes are shown as blank circles and those that are anodes are shown as cross-hatched circles.

Once the spatial spread of activation was quantified for every stimulation setting through a set of parameters describing each 2D outline/shape, artificial neural networks were used to model the complex relationships between the electrode parameters (stimulation settings and configurations) and the optimally fit ellipsoid shape that represents the volume of activation. Two feed-forward artificial neural networks (ANNs) were trained using the activation spreads and the associated set of electrode parameters as the training data.

The ANNs were used to design a predictor function of the form $P=wI+b$, which linearized the complex non-linear relationships between stimulation settings (I) and the equation parameters (P) describing the 3D tissue activation, where w and b represent the weights and biases, respectively. The ANN finds the set of weights and biases mapping these inputs to their corresponding outputs. The first ANN was used to calculate the vertical and lateral spread of activation for each active region. The second ANN was used to calculate the vertical center of each active region. Because the model was axi-symmetric, the 2D boundaries of activation could be swept along the major axis of the virtual electrode to generate 3D volumes of tissue activated. Use of the ANNs allowed interpolation between stimulation settings that were not explicitly analyzed through the FEM solutions and NEURON simulations. This allowed selection of any stimulation setting within the parameter space to generate a 3D VTA within the brain.

Each artificial neural network was created using MATLAB's neural network toolbox (Mathworks Inc., Natick, Mass.). Each network received 12 inputs: stimulation parameter set, pulse-width, encapsulation conductivity, contact configuration, voltage amplitude, and Boolean flags (1=active, 0=inactive) describing the electrode configuration (i.e., active contacts). Each ANN also included one hidden layer with 20 neurons using a sigmoid transfer function and a linear output layer. The first neural network had eight outputs (radial and vertical spread of simulation for each active region) and the second neural network had four outputs (ellipsoid center along the electrode shaft for each active region).

Both neural networks were trained using the Levenberg-Marquardt algorithm on a random sampling of 70% of the stimulation settings and their corresponding ellipsoid parameters. The remaining 30% of the data were used for validation and assessing the performance of the neural networks. The initial weights of each ANN were initialized randomly, and the stopping criteria used to terminate training included a mean squared error less than $10^{-5}$ or up to 500 epochs.

With the predictor function, it is possible to calculate the ellipse equation parameters that defined the volume of tissue activation for a wide range of multipolar electrode configurations and stimulation settings. The input (I) consisted of 12 values:

$$I = \lfloor PW, \sigma_{encap}, n, V, c_0, c_1, c_2, c_3, e_0, e_1, e_2, e_3 \rfloor,$$

where PW is the pulse-width, $\sigma_{encap}$ is the conductivity of the tissue encapsulation layer surrounding the electrode (dynamically based on patient-specific impedance values), n is the configuration number for the specific stimulation settings, V is the voltage amplitude, $c_{0-3}$ are the explicit contact configurations (0 if dormant, −1 if cathode, and +1 if anode), and $e_{0-3}$ are the active ellipsoids generated based upon the active contact configurations using a pseudo-algorithm as follows: * Set $e_{0-3}$ to 1 if the corresponding $c_{0-3}$ contacts are active; * If there are no anodes in contacts $c_{0-3}$, then determine if there are adjacent cathodes; * If there are adjacent cathodes, then set 1 to the active $e_{0-3}$ corresponding to the lowest adjacent cathode contact(s) and 0 to the active $e_{0-3}$ corresponding to the higher adjacent cathode contact(s). This pseudo-algorithm demonstrates an example of how adjacent active regions can be combined if any overlap is present.

The ellipse parameters were solved using weights and biases calculated for each electrode type by the artificial neural networks. The inputs of the ANN were normalized to the range ±1 prior to calculation of the outputs. The normalized inputs ($I_{norm}$) were defined by:

$$I_{norm} = \frac{2 \times I - I_{max} - I_{min}}{I_{max} - I_{min}},$$

where $I_{max}$ and $I_{min}$ are matrices containing the extreme maximum and minimum values of each input parameter, respectively.

The calculation of the normalized output ($O_{norm}$) was performed using the generalized sigmoid-based equation:

$$O_{norm} = \frac{W_{layer}}{1 + e^{-(W_{input} \times I_{norm} + b_{input})}} + b_{layer},$$

where $W_{layer}$ and $W_{input}$ are the layer and input weights, respectively, and $b_{layer}$ and $b_{input}$ are the layer and input biases, respectively. The final output (O) was defined as:

$$O = \frac{O_{norm} \times (T_{max} - T_{min}) + T_{max} + T_{min}}{2},$$

where $T_{max}$ and $T_{min}$ are matrices containing the extreme maximum and minimum values of each output parameter, respectively. The output was an 8×1 (network 1) or 4×1 (network 2) matrix containing the parameters for the parametric equation. For example, in the case of the equation for an ellipsoid of the form $x^2/a^2 + y^2/b^2 + z^2/c^2 = 1$, the a and c parameters for each active ellipse, and the z center of each active ellipse, respectively. The VTAs were visualized in 3D along with their appropriate virtual electrode using the SCIRun/BioPSE visualization environment.

In certain embodiments, the present invention provides a computer-implemented method for determining the volume of activation of neural tissue. The method uses one or more parametric equations that define a volume of activation. The parameters of the parametric equations are given as a function of an input vector. As explained above, the input vector may include stimulation parameters and/or electrode configuration parameters. Also as explained above, examples of such stimulation parameters include voltage or current amplitude, frequency, pulse width, and pulse shape. Also as explained above, the electrode configuration parameters can define structural characteristics of the electrode, such as its dimensions (e.g., height and diameter of the electrode contacts) or the spacing or distribution of the electrode contacts. Also as explained above, the parametric equations may represent various geometric shapes, such as ellipsoid shapes (including super-ellipsoid shapes). In some cases, the function defining the parameters of the parametric equation may be a linear function of the input vector. In other cases, the function defining the parameters of the parametric equation may be a non-linear function of the input vector.

The desired stimulation parameters and/or electrode configuration parameters are received as input data. The values in the input data are used to define the input vector for the function. For example, the input data may include values for pulse width, encapsulation tissue conductivity, voltage, and electrode contact configuration, and these values are used to define the corresponding variables in the input vector. The output of the function can then be calculated, which is then used to define the parameters of the parametric equation. For example, in the case of a parametric equation for an ellipse ($x^2/a^2 + y^2/b^2 + z^2/c^2 = 1$), the output of the function can define the parameters of the ellipse. This parametric equation can then be solved for the volume of activation as an ellipsoid shape. Thus, this method allows for the volume of activation to be calculated directly from the solution to the parametric equation.

As explained above, the parametric equation used to calculate the volume of activation can be obtained using a computational training algorithm, such as an artificial neural network. In particular, the computational training algorithm can be used to design a function that correlates different stimulation parameters and/or electrode configuration parameters to the volumes of activations (i.e., the training data set) produced by the different stimulation parameters and/or electrode configuration parameters.

This training data set can be obtained by coupling an electric field model to a neural tissue model to obtain volumes of activation for multiple different sets of stimulation parameters and/or configurations. Examples of how an electric field model can be coupled to a neural tissue model to calculate a volume of activation are described in U.S. Pat. No. 7,346,382

(McIntyre et al.), U.S. Patent Application Publication No. 2007/0288064 (Butson et al.), and U.S. Patent Application Publication No. 2009/0287271 (Blum et al.), which are all incorporated by reference herein.

As explained above, in some cases, these volumes of activation can be fit to a geometric shape defined by a parametric equation. Also as explained above, this fitting of the volume of activation can be performed using an optimization algorithm. Thus, with this information, the training set may include multiple different sets of electrode parameters (stimulation settings and configurations) and the parameters for the parametric equation (s) that represent the geometric shapes that has been fitted to the volumes of activation associated with set of electrode parameters.

Figure 10:
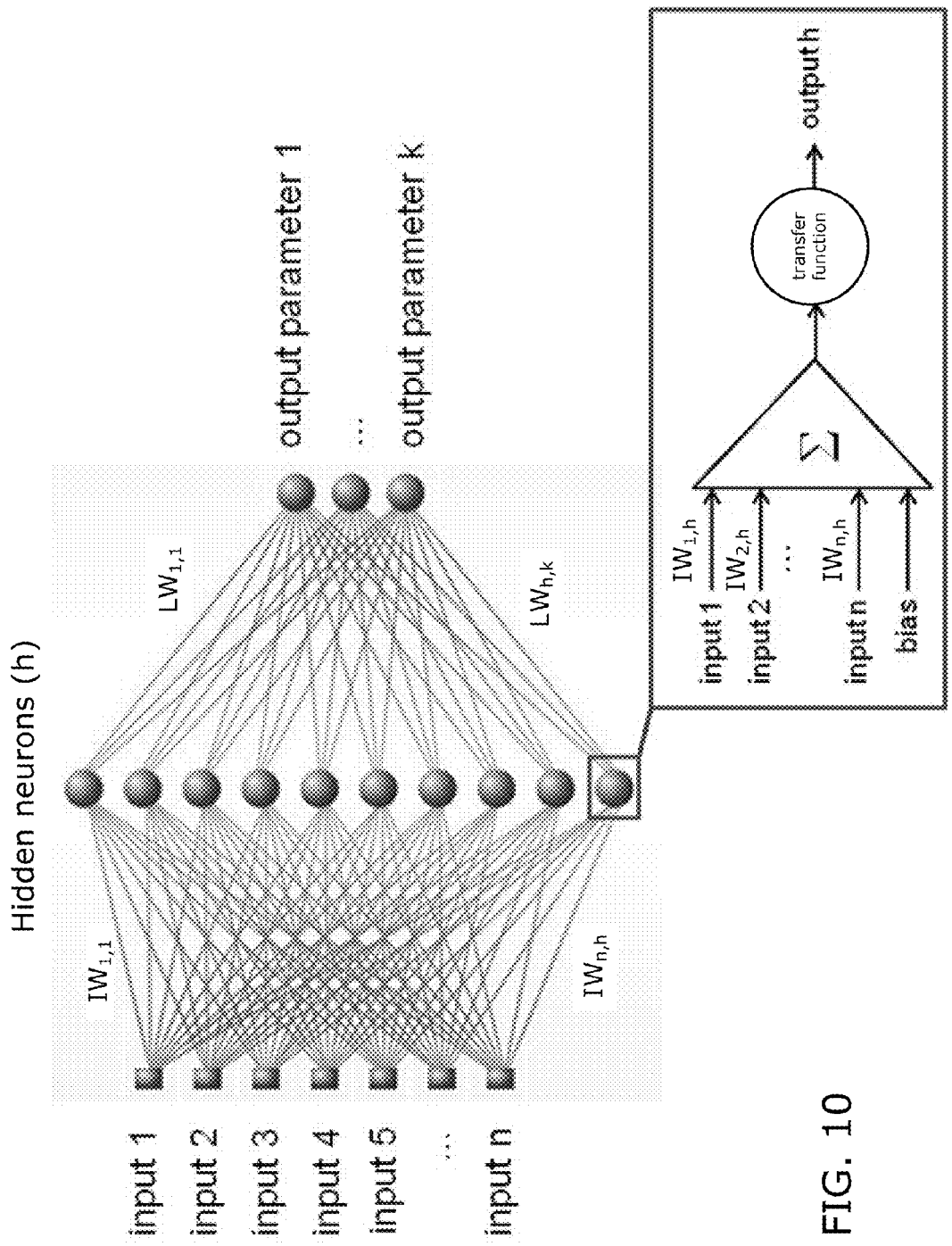
FIG. 10 depicts another example of an artificial neural network that can be used in the present invention.

As explained above, in some cases, the computational training algorithm uses an artificial neural network. The artificial neural network may be used to infer the mapping between the electrode parameters and the parameters of the parametric equation for the geometric shape that has been fitted to the volume of activation that is associated with set of electrode parameters. Using this training data set as the input, the output of the artificial neural network can be used to design a function that maps this relationship. An example of an artificial neural network that can be used in the present invention is shown in FIG. 10. This artificial neural network has three layers: an input layer (the nodes on the left), an output layer (the nodes on the right), and an intermediate, hidden neuron layer (the nodes in the middle). The inset shows how the weights ($W_{n,h}$) and biases are used to change the parameters of the throughput and vary the neural connections in the neural network.

In certain embodiments, the present invention provides a method for determining a function that outputs the parameters of one or more parametric equations that define a volume of activation. The method comprises having an electric field model of an electrode and a neural tissue model. By coupling the electric field model to the neural tissue model as explained above, volumes of activation can be obtained for multiple different sets of stimulation parameters and electrode configuration parameters. A geometric shape (e.g., an ellipsoid), which is defined by one or more parametric equations, is fitted to the volumes of activation. As explained above, this may be performed using an optimization algorithm.

Also as explained above, a computational training algorithm may be used to design a function that correlates the different sets of stimulation parameters and electrode configuration parameters to the parameters for the one or more parametric equations that represent the geometric shapes that are fitted to the volumes of activation. Having designed such a function, this function may be incorporated into computer software (embodied as non-transitory computer-readable storage medium) that comprises instructions for determining the volume of activation using one or more parametric equations whose parameters are given as the function of an input vector that includes stimulation parameters and/or electrode configuration parameters.

Computing Environment

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other processor-based apparatus provide steps for implementing the functions specified in the block or blocks.

Figure 7:
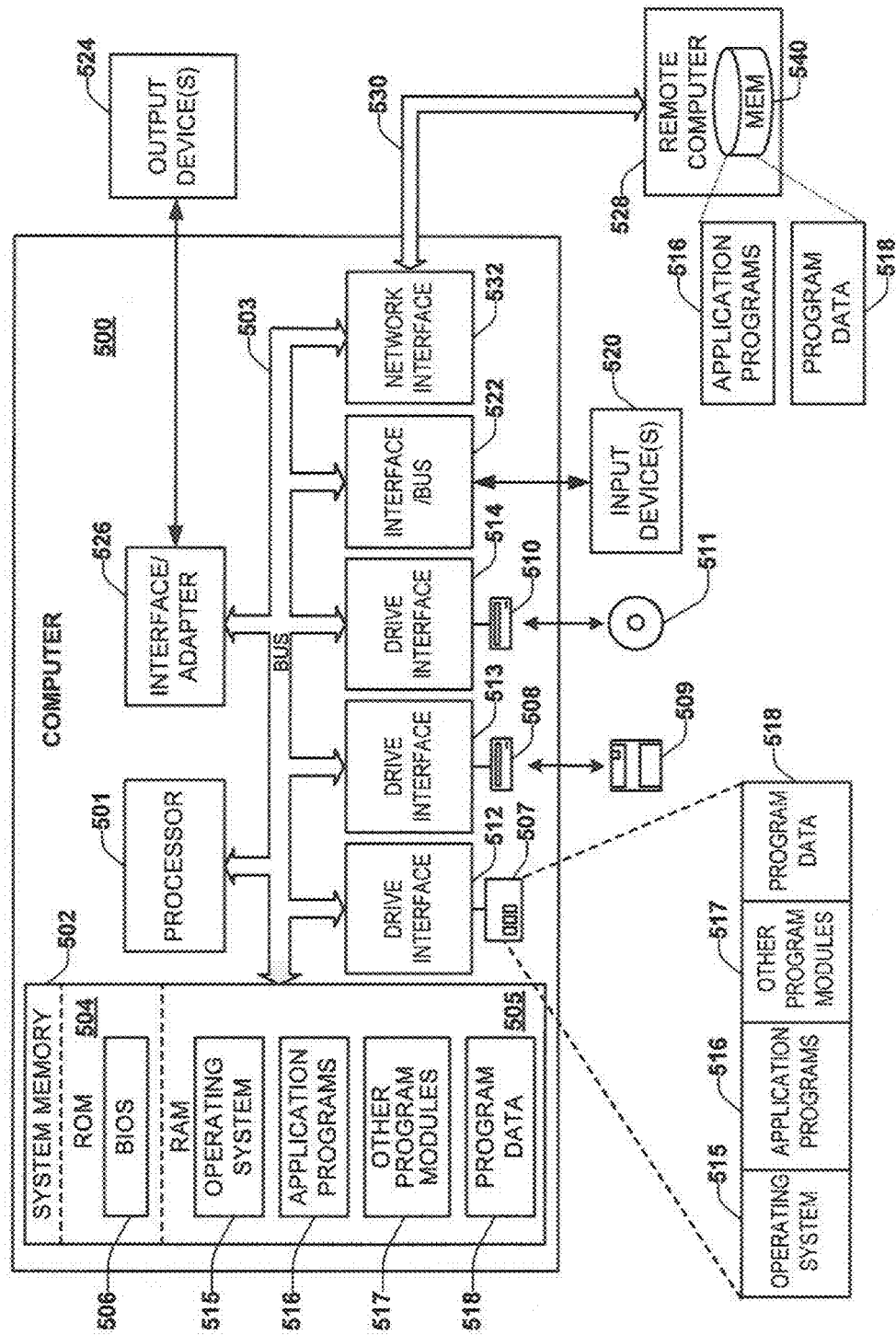
FIG. 7 depicts an example computer environment that can be used to perform methods and processes according to an aspect of the invention.

In this regard, FIG. 7 illustrates one example of a computer system 500 that can be employed to execute one or more embodiments of the invention by storing and/or executing computer executable instructions. Computer system 500 can be implemented on one or more general purpose networked computer systems, embedded computer systems, routers, switches, server devices, client devices, various intermediate devices/nodes or stand alone computer systems. Additionally, computer system 500 can be implemented on various mobile clients such as, for example, a personal digital assistant (PDA), laptop computer, pager, and the like, provided it includes sufficient processing capabilities.

Computer system 500 includes processing unit 501, system memory 502, and system bus 503 that couples various system components, including the system memory, to processing unit 501. Dual microprocessors and other multi-processor architectures also can be used as processing unit 501. System bus 503 may be any of several types of bus structure including a memory bus or memory controller, a peripheral bus, and a local bus using any of a variety of bus architectures. System memory 502 includes read only memory (ROM) 504 and random access memory (RAM) 505. A basic input/output system (BIOS) 506 can reside in ROM 504 containing the basic routines that help to transfer information among elements within computer system 500.

Computer system 500 can include a hard disk drive 507, magnetic disk drive 508, e.g., to read from or write to removable disk 509, and an optical disk drive 510, e.g., for reading CD-ROM disk 511 or to read from or write to other optical media. Hard disk drive 507, magnetic disk drive 508, and optical disk drive 510 are connected to system bus 503 by a hard disk drive interface 512, a magnetic disk drive interface 513, and an optical drive interface 514, respectively. The drives and their associated computer-readable media provide nonvolatile storage of data, data structures, and computer-executable instructions for computer system 500. Although the description of computer-readable media above refers to a hard disk, a removable magnetic disk and a CD, other types of non-transitory computer-readable media that are readable by a computer, such as magnetic cassettes, flash memory cards, digital video disks and the like, in a variety of forms, may also be used in the operating environment; further, any such media may contain computer-executable instructions for implementing one or more parts of the invention. The term "non-transitory computer-readable storage medium" encompasses all computer-readable storage media, with the sole exception being a transitory, propagating signal.

A number of program modules may be stored in drives and RAM 505, including operating system 515, one or more application programs 516, other program modules 517, and program data 518. The application programs and program data can include functions and methods programmed to train a neural network, provide a neural network or otherwise enable a user to interact with or interface with the network via a user interface, such as shown and described herein.

A user may enter commands and information into computer system 500 through one or more input devices 520, such as a pointing device (e.g., a mouse, touch screen), keyboard, microphone, joystick, game pad, scanner, and the like. For instance, the user can employ input device 520 to edit or modify a domain model. Additionally or alternatively, a user can access a user interface via the input device to create one or more instances of a given domain model and associated data management tools, as described herein. These and other input devices 520 are often connected to processing unit 501 through a corresponding port interface 522 that is coupled to the system bus, but may be connected by other interfaces, such as a parallel port, serial port, or universal serial bus (USB). One or more output devices 524 (e.g., display, a monitor, printer, projector, or other type of displaying device) is also connected to system bus 503 via interface 526, such as a video adapter.

Computer system 500 may operate in a networked environment using logical connections to one or more remote computers, such as remote computer 528. Remote computer 528 may be a workstation, computer system, router, peer device, or other common network node, and typically includes many or all the elements described relative to computer system 500. The logical connections, schematically indicated at 530, can include a local area network (LAN) and a wide area network (WAN).

When used in a LAN networking environment, computer system 500 can be connected to the local network through a network interface or adapter 532. When used in a WAN networking environment, computer system 500 can include a modem, or can be connected to a communications server on the LAN. The modem, which may be internal or external, can be connected to system bus 503 via an appropriate port interface. In a networked environment, application programs 516 or program data 518 depicted relative to computer system 500, or portions thereof, may be stored in a remote memory storage device 540.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A computer-implemented method for determining a volume of activation of neural tissue, comprising:
    receiving input data that includes values for stimulation parameters;
    defining an input vector using the input data;
    applying the input vector to a function that is generated from a computational training algorithm;
    obtaining, as output of the function and based on the applied input vector, a set of variable values for a parametric equation that includes a set of variables arranged in a relationship that defines a geometrical shape category that results regardless of values plugged into the set of variables, wherein each of the variables corresponds to a geometric feature of the geometrical shape category, such that different plugged in values for the respective variable results in different characteristics for the respective geometric feature;
    setting the variables of the parametric equation to the obtained variable values to produce a volume of activation corresponding to the stimulation parameters; and
    displaying the calculated volume of activation on a display screen.

2. The method of claim 1, wherein equation values are given as a linear function of the input vector.

3. The method of claim 1, wherein the input vector further includes electrode configuration parameters, and wherein the input data further includes values for the electrode configuration parameters.

4. The method of claim 1, wherein the geometric shape category is an ellipsoid.

5. The method of claim 1, wherein the volume of activation is obtained from the coupling of an electric field model of an electrode inserted into neural tissue to a neural tissue model.

6. The method of claim 1, wherein the computational training algorithm uses one or more artificial neural networks.

7. The method of claim 1, wherein the input vector includes one or more of pulse width, electrode contact impedance, encapsulation tissue conductivity, voltage, or electrode contact configuration.

8. The method of claim 1, wherein the calculated volume of activation is obtained as a shape defined by the parametric equation whose variables are set to the obtained variable values.

9. A computer system comprising:
    a computer processor that is programmed to perform steps, the steps including:
        receiving input data that includes values for stimulation parameters;
        defining an input vector using the input data;
        applying the input vector to a function that is generated from a computational training algorithm;
        obtaining, as output of the function and based on the applied input vector, a set of variable values for a parametric equation that includes a set of variables arranged in a relationship that defines a geometrical shape category that results regardless of values plugged into the set of variables, wherein each of the variables corresponds to a geometric feature of the geometrical shape category, such that different plugged in values for the respective variable results in different characteristics for the respective geometric feature; and
        setting the variables of the parametric equation to the obtained variable values to produce a volume of activation corresponding to the stimulation parameters.

10. A non-transitory computer-readable storage medium comprising instructions for:
    receiving input data that includes values for stimulation parameters;
    defining an input vector using the input data;
    applying the input vector to a function that is generated from a computational training algorithm;
    obtaining, as output of the function and based on the applied input vector, a set of variable values for a parametric equation that includes a set of variables arranged in a relationship that defines a geometrical shape category that results regardless of values plugged into the set of variables, wherein each of the variables corresponds to a geometric feature of the geometrical shape category, such that different plugged in values for the respective variable results in different characteristics for the respective geometric feature; and setting the variables of the parametric equation to the obtained variable values to produce a volume of activation corresponding to the stimulation parameters.

11. A method for determining a function that outputs values for a parametric equation that defines a volume of activation, comprising:

having an electric field model of an electrode and a neural tissue model;

coupling the electric field model to the neural tissue model to obtain volumes of activation for multiple different sets of stimulation parameters and electrode configuration parameters;

fitting a geometric shape to the volumes of activation, wherein the geometric shape is defined by a parametric equation; and using a computational training algorithm to design a function that correlates the different sets of stimulation parameters and electrode configuration parameters to the variables of the parametric equation that represents the geometric shapes that are fitted to the volumes of activation, wherein:

the parametric equation includes a set of variables arranged in a relationship that defines a geometrical shape category that results regardless of values plugged into the set of variables;

each of the variables corresponds to a geometric feature of the geometrical shape category, such that different plugged in values for the respective variable results in different characteristics for the respective geometric feature; and the function is configured to receive input of data representing stimulation parameters and output, based on the received input, a set of variable values for plugging into the variables of the parametric equation.

12. The method of claim 11, wherein the fitting of the geometric shape is performed using an optimization algorithm.

13. The method of claim 11, wherein the geometric shape is an ellipsoid.

14. The method of claim 11, wherein the computational training algorithm uses one or more artificial neural networks.

15. A non-transitory computer-readable storage medium comprising instructions for determining a volume of activation using a parametric equation whose variable values are given as a function of an input vector that includes stimulation parameters and electrode configuration parameters, wherein the function is obtained by the method of claim 11.

16. A computer-implemented method comprising:

providing a volume of tissue activation (VTA) estimator that includes an artificial intelligence trained function configured to output, based on a set of input parameters, variable values for plugging into variables of a parametric equation to produce a geometric shape corresponding to an estimated volume of tissue activation (VTA) for the set of input parameters, wherein:

the parametric equation includes a set of variables arranged in a relationship that defines a geometrical shape category that results regardless of values plugged into the set of variables;

each of the variables corresponds to a geometric feature of the geometrical shape category, such that different plugged in values for the respective variable results in different characteristics for the respective geometric feature; and the input parameters include stimulation parameters and configuration parameters relating to configuration of electrode contact configurations; and employing the VTA estimator to determine an estimated VTA for input parameters for which no simulations or clinical studies have been performed.

17. The method of claim 16, further comprising correlating the estimated VTA with a target VTA to provide an indication of theoretically optimal stimulation parameter settings for a given patient.

18. The method of claim 1, wherein:

the parametric equation includes the following equation:

$$\frac{x^2}{a^2} + \frac{y^2}{b^2} + \frac{z^2}{c^2} = 1;$$

'x', 'y', and 'z' refer to axes in a three-dimensional coordinate system;

'a' and 'b' represent equatorial radii; and

'c' represents a polar radius.

19. The method of claim 1, wherein:

$$\left(\left|\frac{x}{A}\right|^r + \left|\frac{y}{B}\right|^r\right)^{t/r} + \left|\frac{z}{C}\right|^t \leq 1;$$

the parametric equation includes the following equation:

'x', 'y', and 'z' refer to axes in a three-dimensional coordinate system;

'A' and 'B' represent equatorial radii;

'C' represents a polar radius; and

't' and 'r' represent an amount of flattening, respectively, at tips and at an equator.

20. The method of claim 1, wherein:

the parametric equation includes the following equations:

$x^4 + 2x^2y^2 + 4y^4 - x^3 - 6x^2 - xy^2 = 0;$ $y^2 = p(x-a)(x-b)(x-c);$ and $r(t) = \sin^3 t + \cos^3 t;$ 'x' and 'y' refer to axes in a coordinate system;

'a' and 'b' represent equatorial radii;

'c' represents a polar radius; and

't' and 'r' represent an amount of flattening, respectively, at tips and at an equator.

21. The method of claim 1, wherein the parametric equation includes a plurality of parametric equations.

* * * * *